United States Patent [19]
Underwood et al.

[11] Patent Number: 5,292,541
[45] Date of Patent: Mar. 8, 1994

[54] BROWNING MATERIALS DERIVED FROM THE PYROLYSIS OF SUGARS AND STARCHES

[75] Inventors: Gary L. Underwood; John A. Stradal, both of Manitowoc, Wis.

[73] Assignee: Red Arrow Products Company Inc., Manitowoc, Wis.

[21] Appl. No.: 674,442

[22] Filed: Mar. 27, 1991

Related U.S. Application Data

[63] Continuation-in-part of Ser. No. 535,735, Jun. 8, 1990, abandoned, which is a continuation-in-part of Ser. No. 498,849, Mar. 26, 1990, abandoned, and a continuation-in-part of Ser. No. 416,963, Oct. 4, 1989, Pat. No. 5,039,537, and a continuation-in-part of Ser. No. 358,650, May 26, 1989, Pat. No. 4,994,297.

[51] Int. Cl.⁵ ............................................. A23L 1/03
[52] U.S. Cl. .................................. 426/250; 426/271; 426/431; 426/540; 426/652; 426/655
[58] Field of Search ............... 426/650, 655, 520, 524, 426/431, 314, 315, 534, 652, 250, 540, 235, 271

[56] References Cited

U.S. PATENT DOCUMENTS

| | | |
|---|---|---|
| 3,106,473 | 10/1963 | Hollenbeck . |
| 3,330,669 | 7/1967 | Hollenbeck . |
| 3,505,407 | 4/1970 | Cavitt . |
| 3,618,588 | 11/1971 | Amwar et al. ............... 426/540 |
| 3,806,609 | 4/1974 | Goblik et al. . |
| 4,218,487 | 8/1980 | Jaeggi ............................ 426/533 |
| 4,359,481 | 11/1982 | Smits et al. . |
| 4,431,032 | 2/1984 | Nicholson . |
| 4,431,033 | 2/1984 | Nicholson . |
| 4,496,595 | 1/1985 | Nicholson . |
| 4,504,500 | 3/1985 | Schneck et al. . |
| 4,504,501 | 3/1985 | Nicholson . |
| 4,504,507 | 3/1985 | Nicholson . |
| 4,505,939 | 3/1985 | Chiu . |
| 4,525,397 | 6/1985 | Chiu . |
| 4,614,662 | 9/1986 | Ramaswamy ................. 426/540 |
| 4,657,765 | 4/1987 | Nicholson et al. . |
| 4,717,576 | 6/1988 | Nicholson et al. . |
| 4,876,108 | 10/1989 | Underwood et al. . |
| 4,883,676 | 11/1989 | Sophianopoulos et al. . |
| 4,938,868 | 7/1990 | Nelson . |
| 4,973,485 | 11/1990 | Rich ............................... 426/534 |
| 4,994,297 | 2/1991 | Underwood et al. . |

FOREIGN PATENT DOCUMENTS

| | | |
|---|---|---|
| 932686 | 8/1973 | Canada . |
| WO88/00935 | 2/1988 | PCT Int'l Appl. . |
| 1137637 | 12/1968 | United Kingdom . |

OTHER PUBLICATIONS

Pike et al. "Nutrition On Integrated Approach." 3rd Ed. 1984. John Wiley & Sons. New York. p. 22.

Fennema, O. (Edited by)."Food Chemistry." 2nd Ed. 1985. Marcel Dekker, Inc., New York. pp. 98, 586 & 587.

Arseneu et al., "A Study of Reaction Mechanisms by DSC and TG," *Thermal Analysis*, vol. 3, Proceedings Third ICTA Davos, 1971, pp. 319–326.

Bailey, "Inhibition of Warmed-Over Flavor, With Emphasis on Maillard Reaction Products," *Food Technology*, Jun., 1988, pp. 123–126.

Beaumont et al., "Influence of Physical and Chemical Parameters on Wood Pyrolysis," *Ind. Eng. Chem. Process Des. Dev.*, vol. 23, No. 4, 1984, pp. 637–641.

Berg et al., "Characterization of Solids Mixing in an Ultra-Rapid Fluidized Reactor," Paper presented in London, Ontario, Canada, May 12–15, 1986

Berg et al., "Rapid Mixing Studies Between Transported Solids in an Ultra-Rapid Fluidized Reactor," Powder & Bulk Solids Conference, Rosemont, Ill., May, 1985.

(List continued on next page.)

*Primary Examiner*—Donald E. Czaja
*Assistant Examiner*—Anthony Weier
*Attorney, Agent, or Firm*—Marshall, O'Toole, Gerstein, Murray & Borun

[57] ABSTRACT

The invention relates to a process for producing a liquid product for coloring and flavoring a foodstuff by pyrolyzing sugars and starches. The liquid product is useful for imparting a brown smoked color to a foodstuff without adding undesired strong smoked flavors to the foodstuff.

25 Claims, 3 Drawing Sheets

OTHER PUBLICATIONS

Byrne et al., "The Pyrolysis of Cellulose and the Action of Flame Retardants," *J. Appl. Chem.*, vol. 16, Mar., 1966, pp. 81–88.

Collins et al., "Nuclear Magnetic Resonance Spectra of Glycolaldehyde," *J. Chem. Soc. (B)*, 1971, pp. 1352–1355.

Evans et al., "New Approaches to the Study of Cellulose Pyrolysis," *American Chemical Society*, vol. 36, No. 2, 1991, pp. 714–724.

Fenton et al., "Crystalline Clycollic Aldehyde," University Chemical Laboratory, Cambridge.

Glassner et al., "Gas Chromotographic Analysis of Products from Controlled Application of Heat to Paper and Levoglucosan," *Analytical Chemistry*, vol. 37, No. 4, Apr., 1965, pp. 525–527.

Graham et al., "Fast Pyrolysis of Biomass," *Journal of Analytical and Applied Pyrolysis* 6, (1984), pp. 95–135.

Jandera et al., "Ion-Exchange Chromatography of Aldehydes, Ketones, Ethers, Alcohols, Polyols and Saccharides," *Journal of Chromatography*, 98 (1974) pp. 55–104.

Kang et al., "Ketene Formation From the Pyrolysis of Carbohydrates," research paper, Philip Morris Research Center, Richmond, Va., pp. 261–273.

Maga et al., "Pyrazine Composition of Wood Smoke as Influenced by Wood Source and Smoke Generation Variables," *Flavour and Fragrance Journal*, vol. 1, 37–42, (1985).

Martinsson et al., "Partition Chromatography of Sugars on Ion-Exchange Resins," *J. Chromotog.*, 50 (1970) pp. 429–433.

Menard et al., "Characterization of Pyrolytic Liquids from Different Wood Conversion Processes," Fifth Canadian Bioenergy R&D Seminar, undated, pp. 418–434.

Michelsen et al., "Spectroscopic Studies of Glycolaldehyde," *J. Mol. Structure*, 4 (1969) 293–302.

Namiki et al., "A New Mechanism of the Maillard Reaction Involving Sugar Fragmentation and Free Radical Formation," *New Mechanism of Maillard Reaction*, pp. 21–46.

Namiki et al., "Formation of Novel Free Radical Products in an Early Stage of Maillard Reaction," *Prog. Fd. Nutr. Sci.*, vol. 5, pp. 81–91, 1981.

Pecina et al., "High-Performance Liquid Chromatographic Elution Behavior of Alcohols, Aldehydes, Ketones, Organic Acids and Carbohydrates on a Strong Cation-Exchange Stationary Phase," *Journal of Chromatography*, 287 (1984) 245–258.

Piskorz et al., "On the Mechanism of the Rapid Pyrolysis of Cellulose," *Journal of Analytical and Applied Pyrolysis*, 9 (1986) 121–137.

Richards et al., "Influence of sodium chloride on volatile products formed by pyrolysis of cellulose: Identification of hydroxybenzenes and 1-hydroxy-2-propanone as major products," *Carbohydrate Research*, 117 (1983) 322–327.

Roy et al., "The Pyrolysis under Vacuum of Aspen Poplar," paper published in Fundamentals of Thermochemical Biomass Conversion, Edited by R. P. Overend, (1985) pp. 237–256.

Samuelson et al., "Partition Chromatograph of Mixtures Containing Polyols and Carbonyl Compounds (Including Sugars) on Ion Exchange Resins," *Acta Chem. Scand.*, 22 (1968) No. 4, pp. 1252–1258.

Scott et al., Chemical and Fuels from Biomass Flash Pyrolysis, Renewable Energy Branch, Energy Mines and Resource Canada, Ottawa, Canada pp. 12–78 (1988).

Scott et al., "Sugars From Biomass Cellulose by a Thermal Conversion Process," paper published in Energy From Biomass and Wastes XIII Edited by Donald L. Klass, presented at conference in New Orleans Feb. 13–17, 1989, pp. 1349–1363.

Shafizadeh, "Industrial Pyrolysis of Cellulosic Materials," *Applied Polymer Symposium*, No. 28, 153–174 (1975).

Shafizadeh et al., "Pyrolysis of Cellulose," *Carbohydrates Research*, 29 (1973) 113–122.

Stassinopoulou et al., "A Study of the Dimeric Structures of Glycolaldehyde Solutions by NMR," *Tetrahedron.*, vol. 28, pp. 1257–1263 (1972).

Wodley, "Pyrolysis Product of Untreated and Flame Retardant-Treated α-Cellulose and Levoglucosan," Naval Radiological Defense Laboratory, pp. 835–851.

BROWNING MATERIALS DERIVED FROM THE PYROLYSIS OF SUGARS AND STARCHES

CROSS-REFERENCE TO RELATED APPLICATIONS

This application is a continuation-in-part of U.S. Pat. application Ser. No. 07/535,735 filed Jun. 8, 1990, now abandoned, which is a continuation-in-part of Ser. No. 07/498,849 filed Mar. 26, 1990, now abandoned; Ser. No. 07/416,963 filed Oct. 4, 1989, now U.S. Pat. No. 5,039,537; and Ser. No. 07/358,650 filed May 26, 1989, now U.S. Pat. No. 4,994,297.

FIELD OF THE INVENTION

This invention relates to a process for producing liquid products and their use coloring and flavoring foodstuffs. More particularly, this invention is concerned with pyrolyzing sugars and starches to produce a liquid product for coloring and flavoring foodstuffs.

BACKGROUND OF THE INVENTION

Pyrolysis reactions produce a complex and variable mixture of chemicals and include vaporous compounds which are normally liquid at room temperature. Pyrolysis is a general term for the thermal decomposition of any organic material (i.e. wood, plants, fossil fuels etc.) and can occur during a combustion process or in the absence of combustion. In the former, the oxidation or burning of a portion of the organic material provides the heat required to vaporize and decompose the remainder. In the absence of combustion, heat must be supplied indirectly from some other source (i.e. radiation, a solid or gaseous heat carrier, or conduction through reactor walls, etc.).

Pyrolysis of organic material or biomass produces liquids (condensable vapors), gases (non-condensables vapors) and solids (char and ash) in varying proportions depending upon reaction conditions. The pyrolysis liquids can be further subdivided into water-soluble condensable vapors and water insoluble components. It is known that the desirable active ingredients for smoke flavoring are among the water-soluble condensable vapors (liquids).

Use of pyrolysis liquid solutions as a replacement for smoking foodstuffs by direct contact with smoke produced from burning wood has become a standard industry practice. When applied to the surface of meats and other proteinaceous foodstuffs, common pyrolysis solutions not only give the foodstuff a characteristic smoke flavor, but react with the proteins to produce a coloring typical of smoked foodstuffs.

One such commercial liquid smoke preparation is the aqueous liquid smoke flavoring described by Hollenbeck in U.S. Pat. No. 3,106,473. This flavoring product is produced by slow pyrolysis or partial combustion of wood with limited access to air, followed by subsequent solvation of the desirable smoke constituents into water. The water-soluble condensable vapors are used for smoke flavor, while a water-insoluble phase which contains tar, polymers, polycyclic aromatic hydrocarbons including benzo(a)pyrene, waxes and other undesirable products unsuitable for use in food applications is discarded.

Another method of producing liquid solutions for smoke flavoring foods is the fast pyrolysis of wood or cellulose process which is disclosed by Underwood et al. in U.S. Pat. No. 4,876,108. The liquids produced by the fast pyrolysis process are collected and diluted with water to achieve a partial phase separation and to provide an aqueous liquid smoke flavored solution.

Regardless of whether wood or cellulose is pyrolyzed by a slow pyrolysis method or by a fast pyrolysis method the resulting smoke flavored liquid solutions may have a stronger smoke flavoring for some foodstuffs for a given degree of smoke coloring than is desirable for the tastes of some consumers. Even though some consumers prefer a very mild to little smoke flavor, there is still a preference that the flavored foodstuff, especially meat, have the typical full brown color associated with well smoked foodstuffs. Even though a need for such a smoke flavored liquid solution exists none seems to be presently available.

SUMMARY OF THE INVENTION

The present invention provides a high browning, aqueous composition or liquid product that has been derived from a sugar or a starch in which the composition or product has a soluble organic content of less than about 50° Brix, a browning index greater than about 30 and a ratio of titratable acidity to browning index of less than about 0.06. A preferred composition or product has a browning index greater than 50 and more preferably greater than 75. A preferred high browning aqueous composition of this invention is a liquid product derived from pyrolyzed corn syrup having a soluble organic content of about 45° Brix, a browning index of about 104 and a titratable acidity of about 3.2%. The reduced acidity and high browning index provide a liquid product which may be particularly beneficial to color encased foodstuffs such as sausages or other meat products which are prepared by known casing processes.

The present invention also provides a process for producing a high browning liquid product which includes the steps of pyrolyzing a feedstock which is a member of the group consisting of sugar, starch and mixtures thereof to produce a vaporous pyrolysis product; and condensing the vaporous pyrolysis product to produce a water-soluble pyrolysis liquid having little or substantially no smoke flavoring capability.

It is generally advantageous to add sufficient water to dilute the water-soluble pyrolysis liquid phase to reduce its Brix value to about 30° Brix or lower in order to ensure the complete separation of the desired water-soluble components from the undesired water-insoluble components. Specifically, if the Brix value of the water-soluble pyrolysis liquid phase is greater than about 30° Brix, the separation of benzo(a)pyrene from the aqueous layer may be incomplete.

Furthermore, it is also desirable to ensure that the water-soluble liquid phase be less than about 42° Brix when further extracting or treating the water-soluble liquid phase. At Brix values greater than about 42° Brix, subsequent extraction or treatment steps are less effective primarily due to the greater solvating effects of the organic components of the more concentrated solutions.

The resulting water-soluble pyrolysis liquid phase provides a product which is capable of imparting a very full brown color when a sufficient amount is applied to foodstuffs, such as meat and specifically bacon, followed by heating to complete processing of the treated foodstuffs. Furthermore, treatment of a foodstuff with the product leads to a brown colored foodstuff which has little or substantially no smoke flavor or aroma.

The initial water-soluble liquid pyrolysis product described above, and desirably having a maximum Brix value of about 30°, can be further improved by additional treatments to further lower the amounts of flavoring materials in the product. In one treatment the product is extracted with a suitable water-insoluble organic solvent, such as methylene chloride, to remove flavoring materials, especially food flavoring materials which provide smoke flavor and aroma, while retaining those materials which provide browning activity; preferably, hydroxyacetaldehyde which is water-soluble, but quite insoluble or has very little solubility in organic solvents, such as methylene chloride. Generally, suitable extraction solvents include those with a proper range of hydrogen bonding parameters and an appropriate polarity index to solubilize the undesired flavor-supplying organic materials present in the water-soluble product. One suitable alternative solvent is chloroform. After extraction, the organic solvent is then separated from the aqueous phase to yield a food browning liquid product which has little or substantially no flavoring ability.

The water-soluble pyrolysis liquid, with or without a prior extraction with methylene chloride or some other suitable organic solvent, may also be treated with a nonionic resin, cationic resin or a combination of such resins, to also remove undesired contaminants and flavoring materials. The resin treatment of liquid solutions produced by slow pyrolysis of wood is described in U.S. Pat. No. 4,959,232 which is incorporated herein by reference. The conditions disclosed therein are suitable for further processing the water-soluble pyrolysis liquid obtained from a sugar, starch or mixtures thereof, with or without a prior organic solvent extraction. The resulting food browning liquid product has little or substantially no flavoring ability.

After suitable treatment the browning liquid product can be diluted with water or concentrated for appropriate food browning ability depending on the type of application process which is to be used as well as the type of foodstuff which is to be treated.

DETAILED DESCRIPTION OF THE INVENTION

The present invention provides a method for producing useful flavoring and browning products by pyrolyzing sugars and starches.

Some of the sugars which may be suitably pyrolyzed according to the invention are mono-, di- and trisaccharides. Specific sugars and sugary products which can be pyrolyzed are glucose, sucrose, dextrose, invert sugar, galactose, lactose, corn syrup, malt syrups and molasses. Specifically, cow's milk is a well known source of lactose and lactose found in whey is a relatively abundant by-product of the cheese making process. Thus, lactose is a unique readily available sugar that is not derived from plant sources. Due to availability and cost, dextrose, lactose and corn syrups are presently preferred sugars for use in the invention.

Starches which may be pyrolyzed include corn starch, potato starch, wheat starch, oat starch, tapioca starch and rice starch.

The sugar or starch may be pyrolyzed by slow pyrolysis although fast pyrolysis is preferred.

Slow pyrolysis is characterized by relatively slow thermal reactions occurring at moderate temperatures. A typical slow pyrolysis reactor temperature is approximately 420° C. Depending on the method of heating, the temperature gradient in a slow pyrolysis reactor may be from 600° C. at the heat transfer surface to 250° C. at the feedstock surface. Residence times of the solids in the slow pyrolysis reactor may be about one to ten minutes.

The fast pyrolysis process is designed to achieve a very high temperature within a minimum amount of time as well as having a relatively short reactor residence time at the sugar or starch pyrolysis temperature. Short residence times at high temperatures can be achieved in several ways. However, the parameters to be optimized in any fast pyrolysis of a sugar or starch to produce a suitable liquid product in high liquid yields include:

1) High heating rates of the sugar or starch feedstock (greater than 1,000° C. per sec.);
2) Vapor residence times (i.e. the average time that the gas/vapor phase remains in the reactor) greater than about 0.05 sec. and less than about 1.0 sec. and preferably less than 0.6 sec.;
3) Isothermal reaction temperatures between about 400 and 800° C.; and
4) Quenching of the liquid/vapor product to temperatures of less than 300° C. in less than 0.6 sec.

A first fast pyrolysis method, or vacuum pyrolysis method, is based on the principle that primary pyrolysis products can be withdrawn from the reactor under vacuum conditions before they have a chance to react further and produce secondary pyrolysis products. This vacuum pyrolysis method has been described by Roy et al., in "Pyrolysis Under Vacuum of Aspen Poplar," *Fundamentals of Thermo-Chemical Biomass Conversion*, R. P. Overend et al. (editors) Elsevier (publisher) (1985) the contents of which is incorporated herein by reference. In this process, the solid sugar or starch feedstock remains in the reactor until completely reacted and the heating rate of the sugar or starch is much slower than a rapid thermal process or a fluidized bed pyrolysis process, both subsequently described herein. Reactions of primary pyrolysis products to produce secondary pyrolysis products, however, are reduced by quickly removing and cooling the primary pyrolysis vapors. As such, the heating rate is less significant when secondary reactions are limited.

A second fast pyrolysis method, often referred to as "flash" pyrolysis, uses a fluidized bed reactor system operating at a high temperature, generally between 400° and 650° C. Reactor residence times of about 0.5 to about 3 seconds are particularly suitable. (See, e.g., Scott et al., "Production of Liquids from Biomass by Continuous Fast Pyrolysis," *Bioenergy* 84 vol. 3, *Biomass Conversion*, (1984), the contents of which are incorporated herein by reference).

A third fast pyrolysis method, referred to as rapid thermal processing, is a fast pyrolysis method which uses hot particulate solids and/or inert gases to rapidly transfer heat to a feedstock in a reactor system.

These fast pyrolysis methods offer much improved yields and improved quality of liquid products compared to slow, low temperature pyrolysis systems.

The pyrolysis process may be effected using a variety of sugar or starch feedstocks. Pyrolysis of a solid sugar or starch as well as pyrolysis of solutions, syrups or suspensions of a sugar or starch in a solvent or liquid carrier may all be used. Preferably, the type of feedstock will be selected to allow the use of feed systems or injectors which are compatible with specific pyrolysis apparatus and equipment. Further, it is not necessary for the feedstock to be homogenous. Mixtures of impure sugar or starch compositions may all be used as pyrolysis feedstocks provided the additional components or impurities do not interfere with either pyrolysis of the feedstock or isolation of the liquid product or cause problems with the pyrolysis apparatus. Specifically, low nitrogen content whey solutions containing lactose, as well as other byproducts of the cheese making process, may be pyrolyzed.

A wide variety of sugars can be thermally degraded to form a pyrolysis liquid containing the food browning agent hydroxyacetaldehyde (HAA). For example, each of the sugars listed in Table 1 was added to water to make a 5 wt./vol.% sugar solution. Each solution was then injected into a Varian gas chromatograph with an injection port temperature of 250° C. to give pyrolyzed products, including hydroxyacetaldehyde. The amounts of hydroxyacetaldehyde produced from the listed sugars are set forth in Table 1.

TABLE 1

| SUGAR | NUMBER OF CARBON ATOMS | PARTS PER MILLION OF HAA FORMED |
|---|---|---|
| Glyceraldehyde | 3 | 6366 |
| Threose | 4 | 9784 |
| Erythrose | 4 | 12303 |
| Ribose | 5 | 3632 |
| Arabinose | 5 | 2000 |
| Xylose | 5 | 4266 |
| Lyxose | 5 | 18895 |
| Allose | 6 | 1000 |
| Altrose | 6 | 500 |
| Glucose | 6 | 900 |
| Mannose | 6 | <10 |
| Gulose | 6 | 2994 |
| Idose | 6 | 5318 |
| Galactose | 6 | <10 |
| Talose | 6 | 1829 |
| Sorbose | 6 | 3447 |
| Fructose | 6 | 1959 |
| Cellobiose | 12 | <10 |
| Lactose | 12 | <10 |
| Maltose | 12 | <10 |
| Sucrose | 12 | <10 |

While varying amounts of hydroxyacetaldehyde were produced from each of the above-identified sugars, the results listed in Table 1 demonstrate that the observed yield is related to the thermal lability of the sugar. Due to the 250° C. injector port temperature limit in this experiment, only lyxose approached the theoretical maximum yield of two divided by the number of carbons atoms per monosaccharide unit, the lyxose yield being 38%. It can be concluded that nearly all simple sugars can be pyrolyzed to yield varying amounts of hydroxyacetaldehyde at about 250° C.

Both aldoses and ketoses (fructose and sorbose are ketoses, the remaining sugars are aldoses) will pyrolyze to yield hydroxyacetaldehyde. Galactose and mannose are more thermally resistant to pyrolysis to hydroxyacetaldehyde than the other sugars. Neither could be pyrolyzed under the conditions of this experiment at 250° C. Furthermore, additional thermal stability results from the combination of two or more simple sugars in a pyrolyzed molecule as is seen in data for cellobiose, lactose, maltose and sucrose.

Based on the data for glucose and galactose when pyrolyzed independently, it was expected that, on a molar basis, the yield of hydroxyacetaldehyde, a known food browning agent, from lactose would be about half that of glucose. Surprisingly, hydroxyacetaldehyde is formed from the galactose portion of lactose as well as from the glucose portion. Either the epimeric alpha- or beta-form of lactose is suitable as the yield is independent of the type of disaccharide linkage.

While not meant to be a limitation of the mechanism of carbohydrate pyrolysis, it appears that there exists a kinetic bias to cleave lactose between carbons 2 and 3 to yield the two carbon hydroxyacetaldehyde. A mechanism which suggests this bias is reported by Piskorz et al., *J. Anal. Appl. Pyrol.*, 9:121-137 (1986). The observed yield of the pyrolysis products is believed to be a matter of having sufficiently rapid heat transfer for the kinetics of pyrolysis to favor this pathway as opposed to dehydration by other alternate pathways. Short vapor residence times are believed to limit undesired secondary reactions. Furthermore, no oxygen should be present.

The desired liquid products of this invention may be directly applied to a foodstuff using techniques and methods well known in the liquid smoke art. Application techniques such as dipping, spraying, pumping and soaking are all suitable methods for browning a foodstuff with these present liquids.

The liquid product of this invention provides the capability of browning a foodstuff with a minimum concentration of hydroxyacetaldehyde in the liquid product. Suitable concentrations of hydroxyacetaldehyde in a liquid solution required to impart a rich golden brown color to meat when the meat is cooked in a microwave oven are listed in Table 2. To impart color, the solution is applied to the surface of Swift Premium Brown and Serve Sausages by a 2 to 3 second dip. The sausages are then microwaved for one minute along with untreated sausages which serve as controls. After microwaving the sausages are evaluated for visual color appeal. Thus, liquid products having a hydroxyacetaldehyde concentration as low as 0.05% may be used to impart a noticeable golden brown color to sausages.

TABLE 2

| HAA in Solution (Wt./vol. %) | Surface Coating Concentration (μg HAA/cm2) | Total Product Loading (μg HAA/g product) | Color Description |
|---|---|---|---|
| 2.0 | 184 | 350 | Very Brown |
| 1.0 | 92 | 175 | Very Brown |
| 0.5 | 46 | 88 | Golden Brown |
| 0.1 | 9 | 18 | Light Golden Brown |
| 0.05 | 5 | 9 | Very Light Brown |
| 0 | 0 | 0 | Greyish White |

HAA = hydroxyacetaldehyde

In addition to direct application to a foodstuff, the liquid product of this invention may also be applied to foodstuffs indirectly by applying the liquids to sausage and food product casings. The application to casings indirectly allows a processor to impart a brown color to a particular food product.

Any well known method may be used to contact the sausage or foodstuff casing with the liquid product. See, for example, the methods disclosed in U.S. Pat. Nos. 3,330,669 and 4,504,500. Suitable methods for contacting foodstuff casings with the liquid product are also described in U.S. Pat. application Ser. No. 07/416,963 filed Oct. 4, 1989, the relevant portions of that application being incorporated herein by reference.

Food casings suitable for use in the present invention include tubular casings, and preferably tubular cellulosic casings, that are prepared by any of the methods well known in the art. Such casings are generally non-fibrous, flexible, thin-walled seamless casings formed of regenerated cellulose or cellulose ethers, such as hydroxyethyl cellulose, in a variety of diameters. Also suitable are tubular cellulosic casings having a fibrous reinforcing web embedded in the wall of the casings, commonly called fibrous food casings.

The liquid product may be applied to the outer surface of the food casing by passing the casing through a bath of the browning liquid product. The liquid product is generally allowed to soak into the casing before doctoring off any excess liquid by passing the casing through squeeze rolls or wipers for an amount of time sufficient for the casing to incorporate the desired amount of product into the casing. The liquid product may also be externally applied to the casing by methods other than dipping, such as spraying, brushing or roll-coating.

Another method of treating the casing with the liquid product of this invention involves passing a flattened, tubular, cellulose sausage casing over guide rolls through a dip tank which contains the liquid product. The casing passes over additional guide rolls after exiting the dip tank, and then passes between squeeze rolls which minimize any excess carryover of the liquid smoke composition. The total contact time of the casing with the liquid smoke composition in the dip tank, and with excess liquid smoke composition on the casing passing over the guide rolls before the casing passes through the squeeze rolls, typically determines the amount of smoke coloring and flavoring of the liquid smoke composition that the casing will incorporate. The casing is then sent on to conventional further processing, including conventional humidification, as may be required, and conventional shirring.

Alternatively, the liquid product may be applied to the internal surface of the casing by any of several well-known procedures. These include slugging or bubble coating, spraying, and coating while shirring. The slugging method for coating the inside of a casing involves filling a portion of the casing with the coating material, so that the slug or coating material generally resides at the bottom of a "U" shape formed by the casing, and then moving the continuous indefinite length of casing so that the slug of coating material remains confined within the casing, while the casing moves past the slug and is coated on its inside wall by the coating material contained within the slug.

The casing may then be shirred by conventional methods or, prior to shirring, it may be dried or humidified before shirring to a water content suitable for shirring or further processing. The need for conventional drying or humidification after the external liquid treatment depends on the water content of the casing after treatment and the type of casing. If the casing is a non-fibrous casing, a water content within the range of about 8-18 wt.% water immediately before shirring is typical, and for fibrous casing a water content within the range of about 11-35 wt.% water immediately before shirring is typical, where weight percent is based on the total weight of casing including water.

The hydroxyacetaldehyde present in the browning liquid product is also a particularly preferred agent when used with collagen casings because the difunctional hydroxyacetaldehyde is an effective cross-linking agent. Thus, the physical properties of the collagen casings may be improved by the cross-linking provided by hydroxyacetaldehyde.

In the indirect application of the liquid product to sausage or food casings, the lack of a strong or an undesirable flavor is a notable, additional advantage. Conventional liquid smoke products generally must be used at high concentrations to impart enough color or browning to the encased foodstuff. These high concentrations, however, typically have a flavor which is sometimes more intense than desired. The use of the liquid products provided hereby on foodstuff casings allows a processor to achieve the desired brown color without necessarily imparting smoke flavor characteristics to the foods.

BRIEF DESCRIPTION OF THE DRAWING

Details of embodiments of the invention are described by reference to the accompanying drawings in which.

DETAILED DESCRIPTION OF THE DRAWINGS

In the following description the corresponding elements as shown in each figure of the drawings are given the same reference number.

Figure 1:
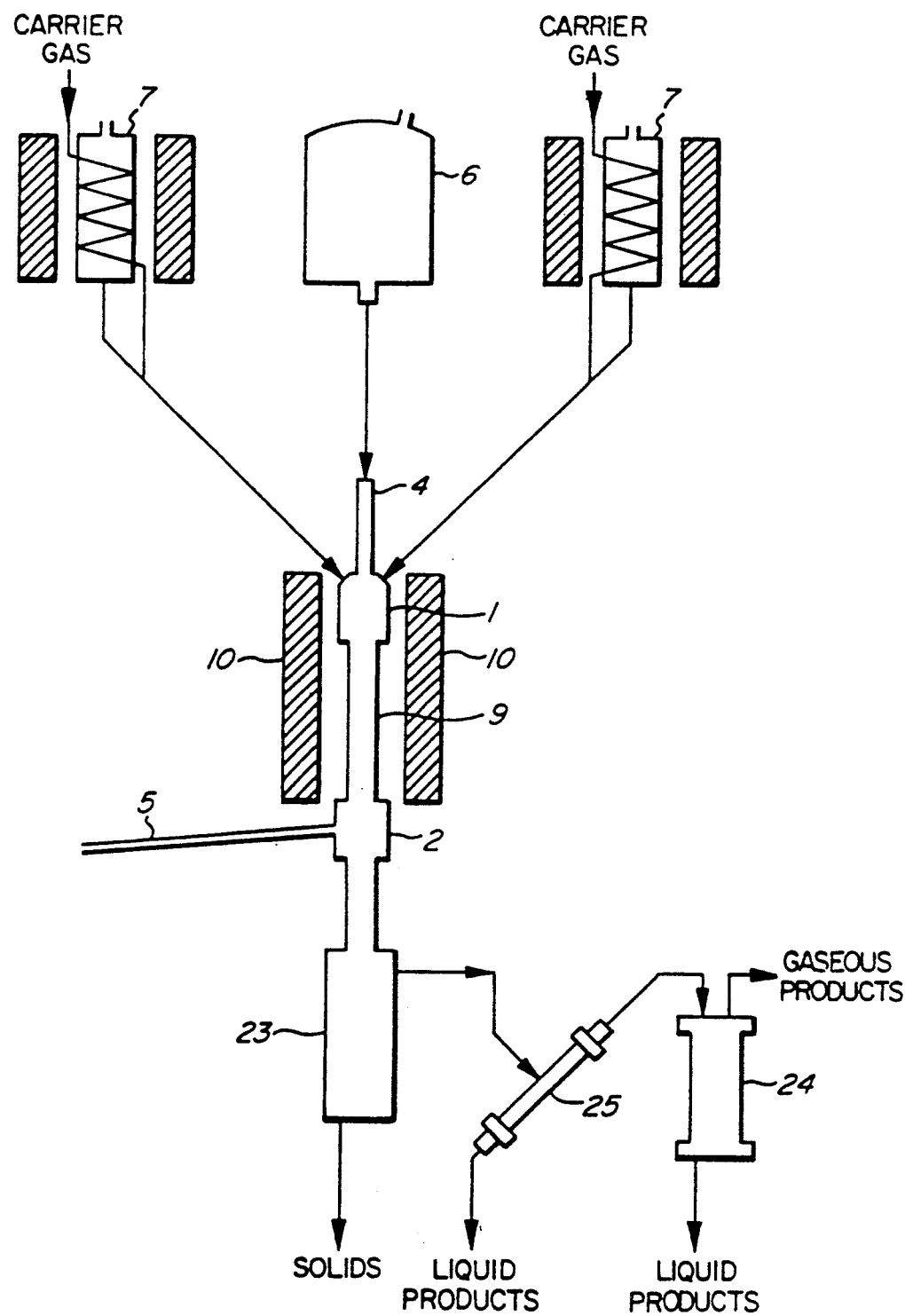
FIG. 1 is a schematic representation of an apparatus useful in a fast pyrolysis method referred to as rapid thermal processing.
Figure 2:
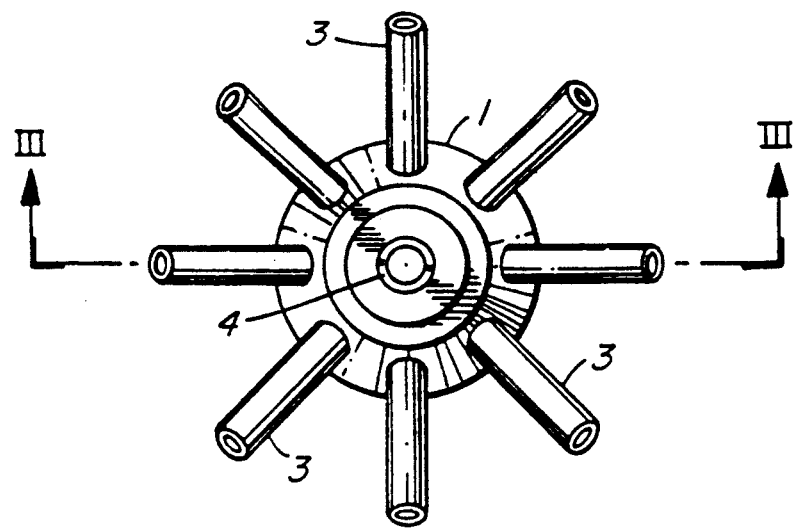
FIG. 2 is a top plan view of the reactor of the pyrolysis apparatus of FIG. 1.
Figure 3:
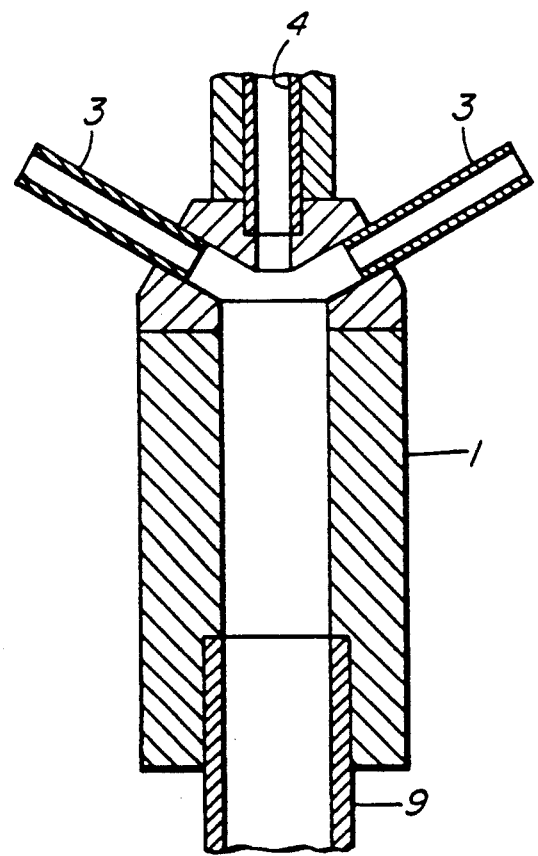
FIG. 3 is a sectional view taken on the line III—III of FIG. 2.

While FIGS. 1 to 3 of the accompanying drawings and the description thereof pertain to Rapid Thermal Processing, similar products can be produced using other fast pyrolysis apparatus and processes, including vacuum pyrolysis and flash pyrolysis as well as other systems that result in a high temperature with a limited residence time.

The major components of the apparatus used in the rapid thermal process are illustrated in FIG. 1. Rapid mixing and heat transfer are carried out in two vessels. The first vessel or thermal mixer (1) allows heat to be transferred to the sugar or starch feedstock from hot inert particulate solids, an inert gas which can be gaseous nitrogen, or a combination of the two. The second vessel or quencher (2) allows fast quenching of the reaction products to prevent the initial pyrolysis products from undergoing secondary reactions.

As shown in FIGS. 2 and 3 the thermal mixer (1) has opposing converging inlets (3) for the heated inert particulates. This system effectively destroys the radial momentum of the particulate heat carrier causing severe turbulence. The particulate feedstock is then injected from the top of the thermal mixer (1) through a cooled tube (4) into the turbulent region where mixing occurs within 30 milliseconds.

After heating and mixing occur, the feedstock and the primary pyrolysis vapors are maintained at the reaction temperature for between 0.03 and 2 seconds. The primary pyrolysis vapors are produced as soon as the feedstock is sufficiently heated to start the pyrolysis reactions. The hot gaseous product is rapidly cooled (i.e. less than 30 milliseconds) by the injection of a single tangential stream of cryogenic nitrogen (5).

Mechanical table feeders may be used to supply the feedstock to the reactor system. The solids pass from sealed hoppers (6) through a double funnel system and are thereby metered onto a rotating table. Two fixed armatures sit near the surface of the rotating table and plough the solids off the outer circumference. The solids then fall from the table into a conical chamber where they are picked up and carried into the transport line by nitrogen gas. The feed rate of the sugar or starch particulate solids is controlled by setting the gap between the lower funnel and the table. Fine control is exercised by the rotation speed of the table.

When inert particulate solids are required to supply the process heat, the feeders (7) send the hot inert particulate solids through a non-mechanical high temperature valve which operates at the reaction temperature. These hot inert particulate solids are then sent on to the thermal mixer (1).

The solid particulate feedstock (or atomized sugar or starch liquid) is then injected into the thermal mixer (1) through a water or air cooled tube (4) into the turbulent region where effective mixing and rapid heating to at least 400° C. occurs within 0.10 second, and preferably within 0.03 second.

Fast pyrolysis of the sugar or starch feedstock (1) continues in a transport reactor (9). The transport reactor is a length of pipe which is indirectly heated using an electrical oven (10) or directly heated by the combustion of natural gas or propane. The mixture of hot gases and feedstock passes from the thermal mixer (1), through the transport reactor (9), to the quencher (2) and to the solids separator (23). With variation of the reactor volume and by manipulating the inert heat carrier/feedstock flow rates, the residence time can be varied between 30 ms and 3 seconds. Reactor temperatures can be set in the range of 400° to 1000° C. Preferable reactor temperatures are between 400° to 800° C. and more preferably between 500° to 600° C. The heating rate that can be achieved with this apparatus is over 10,000° C. per second.

An efficient cyclonic condensor (25) may be used to increase the yield of recovered liquid products. In addition, an electrostatic precipitator (24) can be integrated into a downstream gas line to recover additional liquid products.

After collection of the liquid products, water is added to cause phase separation to reduce benzo(a)pyrene and tars concentration in the liquid product. The amount of water added beyond that necessary to achieve effective phase separation is to some extent a matter of choice. However, it is generally desirable to dilute the raw liquid product with enough water to produce a water-soluble liquid product having a maximum specific gravity of about 30° Brix.

Figure 4:
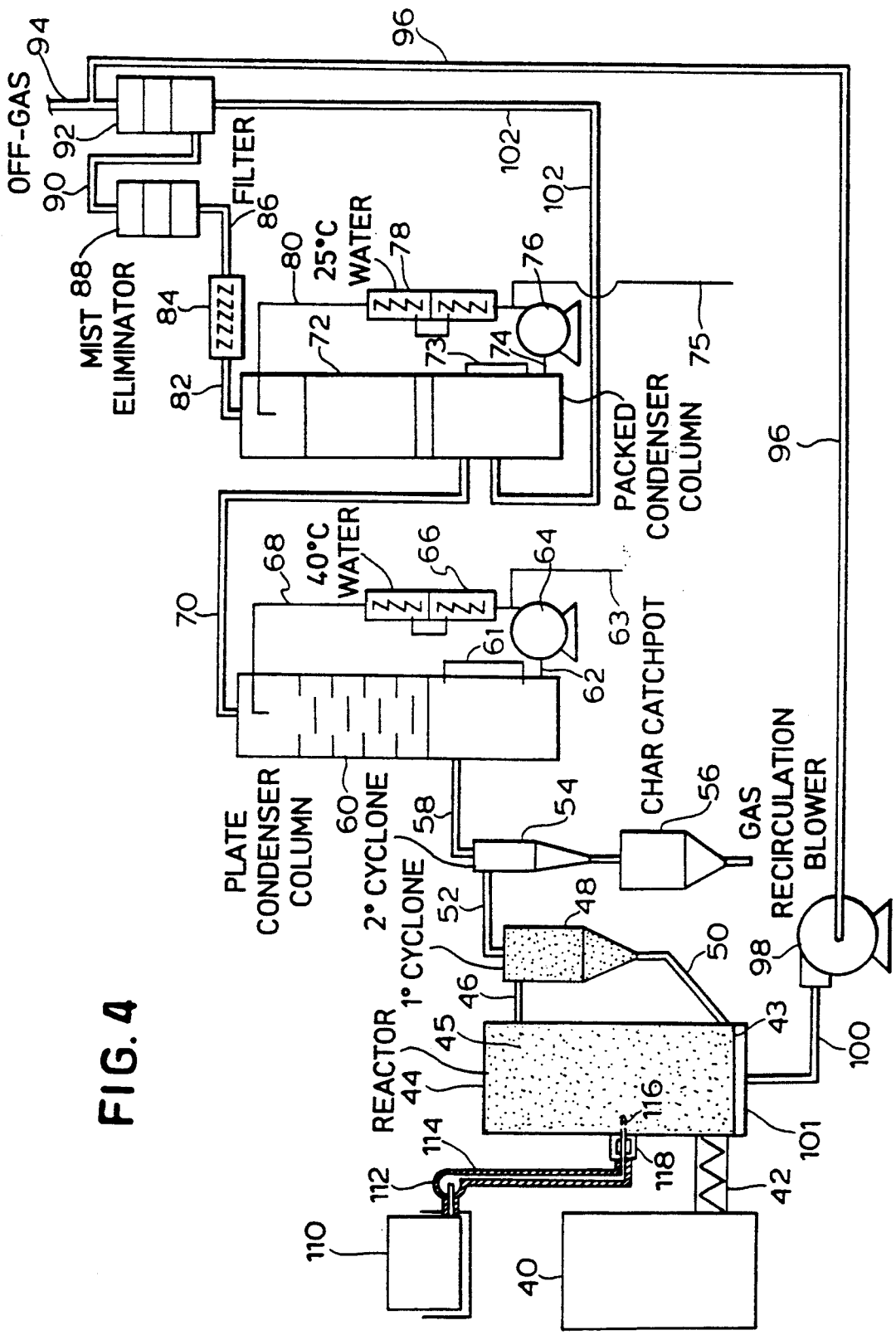
FIG. 4 is a schematic representation of a fast pyrolysis apparatus including an upflow reactor.

FIG. 4 illustrates another apparatus useful for the fast pyrolysis of sugars and starches by the rapid thermal process. Bin (40) stores a supply of the feedstock solid sugar or starch in granular or powder form. The feedstock is removed from the bin (40) by an auger (42) and fed to the lower interior portion of the reactor (44) above a windbox (101) and a grid plate (43). The auger (42) may be water cooled at the inlet to the reactor to prevent premature pyrolysis, which can produce tarry materials. Alternatively, a solution or syrup of a carbohydrate-containing liquid feedstock may be injected into the reactor using a suitable well known injector apparatus. Heated storage tank (110) stores a supply of a liquid feedstock. The liquid feedstock is pumped from the storage tank (110) by a pump (112) through a clean jacketed conduit (114). The liquid feedstock enters the reactor (44) through an injector nozzle (116). The injector nozzle (116) may be cooled at the inlet in the reactor by a water-cooled jacket (118) to prevent premature pyrolysis of the liquid feedstock in the injector nozzle.

A stream of recirculation gas transport fluid is fed by a conduit (100) into the windbox (101), through the grid plate (43) and into the lower portion of the reactor (44) containing a heat transfer medium such as sand (45). Rapid mixing and conductive heat transfer from the sand (45) to the sugar or starch feedstock occurs in the reactor (44). Pyrolytic conversion of the feedstock to a raw product vapor is initiated and continues through the reactor with upward flow into the primary cyclone separator (48). The pyrolysis stream comprising sand (45) and pyrolysis vapor is removed from the reactor (44) by conduit (46) and fed to primary cyclone separator (48). The hot sand (45) is removed from the product vapor stream in the separator (48) and recycled by means of a conduit (50) to the reactor (44). The recycled sand (45) is reintroduced into the lower portion of the reactor (44) at a point above the grid plate (43). Product vapor containing char is withdrawn from the primary cyclone separator (48) by a conduit (52) and fed to a secondary cyclone separator (54) which can be a high efficiency reverse flow cyclone separator. Char and solid sand fines are removed in the secondary cyclone and fed therefrom to a char catchpot (56) for disposal or further handling as desired.

The hot product stream is withdrawn from the top of the secondary separator (54) through a conduit (58) which feeds the vapor comprising condensable and noncondensable components and some fine residual char and ash to the lower interior space of a baffled condenser (60) where the vapor is immediately quenched. The condenser (60) uses the product liquid as the quench medium.

The condensed liquid product is withdrawn from the bottom of the condenser (60) through a conduit (62) and is fed to a pump (64) which pumps it to a heat exchanger (66) indirectly cooled by water. The cooled product liquid is removed from the heat exchanger (66) and returned by conduit (68) to the top of the condenser (60) as a spray. A conventional transparent vertical sight indicator (61) is mounted on the lower part of the first condenser (60). The sight indicator has high and low liquid level marks. When the volume of liquid in the condenser (60) reaches the high level mark raw pyrolysis liquid is withdrawn through a conduit (63) until the liquid level reaches the low level mark. Liquid is then accumulated in the condenser until it reaches the high level mark again when the raw pyrolysis liquid withdrawal step is repeated.

Non-condensed product vapor is withdrawn from the top of the condenser (60) by conduit (70) and is fed to a packed second condenser column (72) where it is further cooled. Liquid is withdrawn by a conduit (74) from the bottom of the packed second condenser and fed to a pump (76) which pumps it through a water cooled heat exchanger (78). Cooled liquid product is removed from the heat exchanger (78) by conduit (80) and is fed to the top of the packed second condenser column (72). A conventional transparent vertical sight indicator (73) is mounted on the lower part of the second condenser (72). The sight indicator has high and low liquid level marks. When the high level mark is reached raw pyrolysis liquid is withdrawn through conduit (75) until the liquid level reaches the low mark.

A vapor stream is removed from the top of the packed second condenser column (72) by a conduit (82) and fed through a water cooled heat exchanger (84) from which it is fed to a conduit (86) which feeds it to a mist eliminator (88). The vapor is fed from the mist eliminator (88) to a conduit (90) which delivers the vapor to a filter (92). Liquid is removed from the bottom of the filter (92) by means of a conduit (102) and recirculated to the bottom portion of the second condenser column (72) above the level of liquid in the column. A portion of the resulting clean by-product gas stream is ducted from the filter (92) by a conduit (94) to waste while a further portion is taken from the conduit (94) and fed to conduit (96) which feeds it to a gas recirculation blower (98). The recirculated gas is fed from the blower (98) to a conduit (100) which feeds it into the bottom of the reactor (44).

The following examples are presented to further illustrate the invention. In the examples, the concentration values for the organic components in the described liquids are given as °Brix values. The °Brix values were obtained using standard refractory techniques which are well known in the sugar industry. The percent weight per volume (% wt./vol.) values for hydroxyacetaldehyde were obtained using gas chromotography and comparing the peak integrations of a sample of a liquid (diluted if necessary) with peak integrations of a standard curve generated from a 1–5% serial dilution of hydroxyacetaldehyde in water. Gas chromatograms were run on a Varian Gas Chromatograph (Model 3300 equipped with a Varian Integrater Model 4290) fitted with a fused-silica capillary column (either a 0.25 mm×60 m J&W DB1701 column or a 0.25 mm×. 30 m J&W DB-Wax column) using hydrogen carrier gas at a flow rate of 2.0 ml/mm and a temperature program of 40° C. initial temperature, zero minute hold followed by increasing the temperature at 8.0° C./minute to 255° C. The injector temperature was 220° C., the detector temperature was 300° C.

Under these conditions, the retention time of hydroxyacetaldehyde in the J&W DB-1701 column was 2.85 minutes and on the J&W DB-Wax column was 4.70 minutes.

EXAMPLE 1

Dextrose (Cerelose ® dextrose 2001, D.E. 95, Corn Products, Inglewood Cliffs, N.J.) was fast pyrolyzed at about 550° C. using an apparatus as illustrated in FIG. 4 with a vapor residence time of 0.7 seconds at a pressure of 1–1.5 psi. The vapors were condensed by direct contact with 20° C. recirculating water. About five pounds of dextrose were fed to the apparatus over a twenty minute period.

The resulting raw pyrolysis liquid was found to have a Brix value of about 4° and to contain about 0.5% wt./vol. hydroxyacetaldehyde. The solution was then concentrated at 50° C. under a water aspirator vacuum of about −28.5 inches of mercury to remove excess water to give a solution of about 63° Brix and a hydroxyacetaldehyde concentration of about 29% wt./vol.

EXAMPLE 2

Powdered dextrose was pyrolyzed in a downflow transport reactor (FIG. 1) using sand as the heat transfer media. The reactor temperature was 600° C. and the vapor residence time in the reactor was 75 msec. The pyrolysis liquid yield was 83.5%, noncondensable gases yield was 14% and char yield was 2.5%. The composition of the condensed raw pyrolysis liquid was as follows:

| Brix | 64.7° |
|---|---|
| Water | 34.3% |
| Hydroxyacetaldehyde | 25.5% |
| Acetol | 2.6% |
| Acetic acid | 1.6% |
| Other organics (including hydroxymethyl furfural) | 36.0% |

EXAMPLE 3

The initial 4° Brix pyrolysis liquid obtained in Example 1 was concentrated by evaporation under reduced pressure to give a 18° Brix solution containing about 5% wt./vol. hydroxyacetaldehyde. A portion of this solution (60 ml) was extracted with three portions of food grade methylene chloride (20 ml) to remove flavor components. The extracted solution was then treated batchwise with two types of food grade resins, first with the Rohm & Haas nonionic resin XAD-4 (6 g) and then with the Rohm & Haas cationic resin IR-120 (3 g) to remove additional flavor constituents. The resulting solution (about 12.9° Brix) was evaporated to about 50° Brix to remove low molecular weight volatile components and residual methylene chloride. The concentrated solution contained about 32% wt./vol. hydroxyacetaldehyde. Subsequently, the concentrate was diluted with water back to 13° Brix, which is a suitable concentration for direct application to a foodstuff.

The 13° Brix solution containing about 5% wt./vol. hydroxyacetaldehyde was applied to the surface of Swift Premium Brown and Serve Sausages (Swift -Eckrich, Inc., Oak Brook, Ill.). The sausages were microwaved along with untreated sausages which were used as a control. After microwaving the sausages treated with the browning solution had a rich golden brown color compared to the untreated control sausages which had a greyish white color. There was no palatable difference in terms of flavor between the two groups of sausages. This shows that the flavorless browning solution browned the sausages without also contributing a detectable flavor to the sausages.

EXAMPLE 4

This example describes a method for producing a high browning, flavorless liquid product from dextrose and its usefulness in browning foods in a microwave oven.

Dextrose was fast pyrolyzed at about 550° C. in an upflow circulating fluidized bed reactor as illustrated shown in FIG. 4. The vapor residence time was about 0.7 second, the pressure was about 114 1.5 psi and the pyrolysis vapors were condensed and solubilized by direct contact with circulating 20° C. water. The resulting aqueous condensate solution contained about 4° Brix total organic solids as determined by refractive index and about 0.5% wt./vol. hydroxyacetaldehyde as determined by gas chromatography. This solution was then concentrated to 18° Brix organic solids by rotary evaporation and was found to contain about 6% wt./vol. hydroxyacetaldehyde. A portion of this solution (60 ml) was then extracted with three portions of food grade methylene chloride (20 ml) to remove flavor components. The solution was then concentrated to 50°

Brix organic solids to remove low molecular weight flavor components. This solution was found to contain 23% wt./vol. hydroxyacetaldehyde by gas chromatography. Gas chromatography analysis also showed that furfural, phenolics, and pyrazines were the major flavor components removed by the extraction and evaporation. Water was then added to dilute the solution back to 5% wt./vol. hydroxyacetaldehyde and the organic solids content was found to be 12° Brix.

This diluted flavorless foodstuff browning solution was applied to the surface of Swift Premium Brown and Serve Sausages. The sausages were microwaved for two minutes along with untreated sausages which were used as a control. After microwaving the sausages treated with the browning solution had a rich golden brown color compared to the control sausages which had a greyish white color. There was no palatable difference in terms of flavor between the two groups of sausages. This shows that the flavorless browning solution browned the sausages without also contributing a detectable flavor to the sausages.

EXAMPLE 5

This example describes a method for producing a high browning, flavorless liquid product from lactose.

Lactose was pyrolyzed in a circulating fluidized bed reactor, capable of processing about 100 lbs/hr of solid feedstock, at 500° C. in an upflow circulating fluidized bed reactor described in connection with FIG. 4. The vapor residence time in the reactor was about 0.7 second, the pressure was about 1-1.5 psi and the pyrolysis vapors were condensed by direct contact with circulating 20° C. water as described in Example 1. The resulting condensate solution, or raw pyrolysis liquid, contained about 2° Brix total organic solids as determined by refractive index. The hydroxyacetaldehyde concentration was 0.11%, the acetic acid content was less than about 0.01% and the acetol content was about 0.06% as determined by analytical gas chromatography. The solution was then concentrated by evaporation at 50° C. under a vacuum of −29 inches mercury to 26° Brix organic solids including 4% wt./vol. hydroxyacetaldehyde. The concentrated solution (60 ml) was extracted with three portions of food grade methylene chloride (20 ml) to remove flavor components such as furfural, phenolics and pyrazines. The extracted solution was then concentrated to 50° Brix organic solids to remove low molecular weight flavor components. This solution was found to be 11% wt./vol. hydroxyacetaldehyde. The solution was then diluted with water back to 5% wt./vol. hydroxyacetaldehyde and was found to contain 19° Brix organic solids.

This diluted flavorless food browning solution was applied to the surface of Swift Premium Brown and Serve Sausages by dipping the sausage into the solution for two to three seconds and then allowing the sausage to drip dry for thirty seconds. The sausages were microwaved along with untreated sausages which were used as a control. After microwaving the sausages treated with the browning solution had a rich golden brown color compared to the control sausages which had a greyish white color. There was no palatable difference in terms of flavor between the two groups of sausages. This shows that the flavorless browning solution browned the sausages without also contributing a detectable flavor to the sausages.

EXAMPLE 6

This example shows a second method for producing a high browning, flavorless liquid solution from dextrose and its usefulness in browning a foodstuff cooked in a microwave oven.

Dextrose was pyrolyzed according to the method of Example 4 and the resulting aqueous solution was concentrated to 18° Brix organic solids and 6% wt./vol. hydroxyacetaldehyde. A portion of this solution (60 ml) was then treated batchwise with two types of food grade resins, first with the Rohm and Haas non-ionic XAD-4 resin (6 grams) and then with the Rohm and Haas cationic IR-120 resin (3 grams) to remove flavor components. The solution after resin treatment was found to contain about 13° Brix organic solids by refractive index. It was then concentrated to about 50° Brix organic solids by evaporation to remove low molecular weight flavor components. Gas chromatography analysis showed that this solution contained 23% wt./vol. hydroxyacetaldehyde and that furfural, phenolics and pyrazines were the major flavor constituents removed by the resin treatment and evaporation. The solution was then diluted back with water to 5% wt./vol. hydroxyacetaldehyde and found to have about 12° Brix organic solids.

This diluted flavorless food browning solution was applied to the surface of Swift Premium Brown and Serve Sausages. The sausages were microwaved along with untreated sausages which were used as a control. After microwaving the sausages treated with the browning solution had a rich golden brown color compared to the control sausages which had a greyish white color. There was no palatable difference in terms of flavor between the two groups of sausages. This shows that the flavorless browning solution browned the sausages without also contributing a detectable flavor to the sausages.

EXAMPLE 7

This example describes removing undesired flavor components from a liquid product of lactose by methylene chloride extraction.

Lactose was fast pyrolyzed according to the method of Example 5. The resulting aqueous liquid product was found to contain about 2° Brix total organic solids by refractive index. This solution was then concentrated by evaporation at 50° C. and −29 inches mercury to about 26° Brix organic solids and then divided into two portions. One of the portions (100 ml) was extracted with food grade methylene chloride (3×30 ml) and a second portion was not extracted so as to serve as a control. The organic solids in the extracted portion dropped from 26° Brix to 22° Brix.

Each solution was then diluted to 150 ppm organic solids with distilled water. A triangular taste panel was set up with the following three samples:
 A=Extracted Diluted Sample
 B=Not Extracted Diluted Sample
 C=Not Extracted Diluted Sample Ten taste panelists were asked to pick the odd sample and comment on the flavors. Seven of the panelists identified Sample A. Comments of the panelists indicated Sample A had virtually no flavor compared to B and C which both had a mild smoky flavor. This demonstrates that the methylene chloride extraction was an effective way to remove flavor components from the lactose pyrolysis liquid.

EXAMPLE 8

This example describes a method of producing a liquid product from starch.

A sample of FRO-DEX-24-D (Amaizo Co., Hammond, Ind.), a powdered starch containing 6% moisture and having a 26% dextrose equivalent content was fast pyrolyzed at about 550° C. in an upflow circulating fluidized bed reactor such as illustrated in FIG. 4. The vapor residence time was about 200 msec. and the pyrolysis vapors were condensed and solubilized using a cold water condenser. The resulting condensate solution was found to contain 51° Brix organic solids by refractive index and 24% wt./vol. hydroxyacetaldehyde by gas chromatography. Thus, the hydroxyacetaldehyde concentration was about 50% of the organic solids of the condensate solution.

EXAMPLE 9

This examples describes another method of producing a liquid product from starch.

A sample of PF powdered starch (Amaizo Co., Hammond, Ind.) containing about 12% moisture was fast pyrolyzed at about 550° C. in an upflow circulating fluidized bed reactor. The vapor residence time was about 200 msec. and the pyrolysis vapors were condensed and solubilized using a cold water condenser. The resulting condensate solution was found to contain 56° Brix organic solids by refractive index and 29% wt./vol. hydroxyacetaldehyde by gas chromatography. Thus, the hydroxyacetaldehyde concentration was about 50% of the organic solid of the condensate solution.

EXAMPLE 10

This example describes a method of producing a high browning, flavorless liquid product from corn syrup.

High dextrose corn syrup having 83.7% total solids and 16.3% moisture (62 D.E./44 Baume' corn syrup, ADM Corn Sweetners Cedar Rapids, Iowa) was heated to about 150° F. and then pumped through steam heated conduits into an upflow circulating fluidized bed reactor illustrated in FIG. 4. The heated corn syrup enter the reactor through a nozzle having a 3/32 inch aperture. The reactor temperature was about 550° C., the vapor resident time was about 700 m sec. and the pressure was about 1.5 psi. The pyrolysis vapors were condensed and solublilized by direct contact with 20° C. recirculating water to give a liquid product having about 30° Brix. The compositions of the liquid product was as follows:

| | |
|---|---|
| Hydroxyacetaldehyde | 16.1% |
| Acetol | 0.81% |
| Acetic Acid | 1.6% |
| Cyclotene | 0.06% |
| Furfural | 0.41% |
| Methanol/Methyl Acetate | 0.83% |
| Maltol | 0.10% |
| Formic Acid | <0.1% |

The 30° Brix solution was extracted with methylene chloride (one volume methylene chloride to ten volumes solution) and then concentrated by evaporation under reduced pressure (−28.5 inches of mercury) at about 50° C. to give a liquid product of about 45° Brix.

EXAMPLE 11

The corn syrup derived liquid product of Example 10 was diluted with water to about 23° Brix and compared to four different pyrolysis liquid samples: 1) a methylene chloride extracted slow pyrolysis commercially available liquid smoke made according to the procedure described in U.S. Pat. No. 4,717,576 to Nicholson (Briefly, CHARSOL C-12, 500 ml 28° Brix, 12% titratable acidity, browning index 12, Red Arrow Products Company Inc. was extracted with methylene chloride, 50 ml, to give a liquid smoke of about 23° Brix); 2) a fast pyrolysis product of Avicel pH 101 cellulose made according to the procedure described in Example 8 of U.S. application Ser. No. 07/416,963 filed Oct. 4, 1989; 3) a fast pyrolysis product of maple sawdust treated by contact with a XAD-4 nonionic resin made according to the procedure described in Example 6 of U.S. application Ser. No. 07/416,963 filed Oct. 4, 1989 and 4) a fast pyrolysis product of dextrose the values were calculated from the data in Example 2, above, in direct proportion to °Brix values.

Comparative physical properties of the five liquid products are illustrated in Table 3.

TABLE 3

| Liquid | °Brix | Titratable Acidity | Browning Index | Titratable Acidity/ Browning Index (B.I.) | Casing Browing* Density B.I./cm² |
|---|---|---|---|---|---|
| CHARSOL C-12 (methylene chloride extracted) | 23 | 11.7 | 10.3 | 1.14 | 0.0151 |
| AVICEL pH 101 | 23 | 1.0 | 16.3 | 0.061 | 0.239 |
| HARDWOOD XAD-4 resin extracted | 23 | 4.5 | 19.4 | 0.23 | 0.284 |
| DEXTROSE | 23 | 1.0 | 47.6 | 0.021 | 0.0697 |
| CORN SYRUP (methylene chloride extracted) | 23 | 1.6 | 53.0 | 0.030 | 0.0776 |

*Values calculated according to the procedures described by Nicholson U.S. Pat. No. 4,717,576

The above data indicated that the liquid product prepared according to Example 10 has a significantly higher casing browning density value compared to commercial liquid smoke treated by the method disclosed by Nicholson. In addition, the pyrolysis of sugars and starches provides a liquid product with a significantly reduced acidity. Such low acidity liquid products are particularly preferred for applications to food casing because casings are susceptible to degradation at low pH values.

The foregoing detailed description has been given for clearness of understanding only, and no unnecessary limitations should be understood therefrom, as modifications will be obvious to those skilled in the art.

What is claimed is:

1. A process for producing a pyrolysis product of sugars, starches or mixtures thereof comprising:
   pyrolyzing a member of the group consisting of sugar, starch and mixtures thereof to produce a vaporous pyrolysis product;
   condensing the vaporous pyrolysis product to produce a water-soluble pyrolysis liquid;

contacting the water-soluble pyrolysis liquid with an organic solvent which is essentially insoluble in water to extract flavoring materials from the water-soluble pyrolysis liquid into the organic solvent; and separating the organic solvent from the so-extracted water-soluble pyrolysis liquid to yield the so-extracted water-soluble pyrolysis liquid as a browning liquid product which has substantially no detectable smoke flavoring ability by taste.

2. A process according to claim 1 in which dextrose is pyrolyzed.

3. A process according to claim 1 in which lactose is pyrolyzed.

4. A method according to claim 1 in which sufficient water is added so that the water-soluble pyrolysis liquid has a specific gravity not significantly higher than 30° Brix.

5. A method according to claim 1 in which the extracted water-soluble pyrolysis liquid is further contacted with a member of the group consisting of a cationic exchange resin, a nonionic exchange resin and mixtures thereof to further remove flavoring materials and produce a browning liquid product which is essentially flavorless but which browns a foodstuff.

6. A method according to claim 1 in which the extracted water-soluble pyrolysis liquid is concentrated to raise its specific gravity for improved foodstuff browning ability.

7. A method according to claim 6 in which the browning liquid product is concentrated to at least 40° Brix.

8. A method according to claim 1 in which the organic solvent is one in which hydroxyacetaldehyde has very little solubility.

9. A method according to claim 8 in which the organic solvent is methylene chloride.

10. A method of browning a foodstuff without imparting strong smoke flavoring to the foodstuff comprising applying the browning liquid product produced by the process of claim 1 to a foodstuff in a sufficient amount to develop an acceptable brown color in the foodstuff.

11. A method according to claim 10 in which the foodstuff is bacon.

12. A method according to claim 1 in which the vaporous pyrolysis product is condensed by direct contact with a colder liquid.

13. A method according to claim 12 in which the colder liquid is water.

14. A method according to claim 13 in which the colder liquid is a mixture of the water-soluble pyrolysis liquid and water.

15. A liquid product for coloring a foodstuff prepared by the method of claim 1.

16. A high browning flavorless aqueous composition derived from vapor of a pyrolyzed material selected from the group consisting of sugar, starch, and mixtures thereof, wherein said composition has a soluble organic content of less than about 50° Brix, a browning index greater than about 30 and ratio of a titratable acidity to browning index of less than about 0.06.

17. The high browning aqueous composition of claim 16 derived from corn syrup having a titratable acidity of about 3.2%, a browning index of about 104 and a soluble organic content of about 45° Brix.

18. The high browning aqueous composition of claim 16 wherein the browning index is greater than about 50.

19. The high browning aqueous composition of claim 18 wherein the browning index is greater than about 75.

20. A high browning flavorless aqueous composition derived from vapor of a pyrolyzed material selected from the group consisting of sugar, starch, and mixtures thereof, wherein said composition has a casing browning density of greater than 0.03.

21. A process for producing a pyrolysis product of sugars, starches or mixtures thereof comprising:
    pyrolyzing a member of the group consisting of sugar, starch and mixtures thereof to produce a vaporous pyrolysis product;
    condensing the vaporous pyrolysis product to produce a water-soluble pyrolysis liquid; and
    contacting the water-soluble pyrolysis liquid with a member of the group consisting of an cationic exchange resin, a nonionic exchange resin and mixtures thereof to remove flavoring materials and thereby produce a browning liquid which has no detectable smoke flavoring ability by taste.

22. A process according to claim 21 in which dextrose is pyrolyzed.

23. A process according to claim 21 in which lactose is pyrolyzed.

24. A method according to claim 21 in which the browning liquid is concentrated to raise its specific gravity for improved foodstuff browning ability.

25. A method according to claim 24 in which the browning liquid is concentrated to at least 40° Brix.

* * * * *

UNITED STATES PATENT AND TRADEMARK OFFICE
CERTIFICATE OF CORRECTION

PATENT NO. : 5,292,541

DATED : March 8, 1994

INVENTOR(S) : Underwood et al.

It is certified that error appears in the above-identified patent and that said Letters Patent is hereby corrected as shown below:

Column 12, line 56, "114 1.5 psi" should be --1-1.5 psi--.

Column 16, line 34, "0.239" should be --0.0239--.

Column 16, line 36, "0.284" should be --0.0284--.

Signed and Sealed this

Seventeenth Day of January, 1995

Attest:

BRUCE LEHMAN

Attesting Officer

Commissioner of Patents and Trademarks